US006825925B2

(12) United States Patent
Yagita

(10) Patent No.: US 6,825,925 B2
(45) Date of Patent: Nov. 30, 2004

(54) INSPECTING APPARATUS FOR FOREIGN MATTER

(75) Inventor: Kiyoshi Yagita, Tokyo (JP)

(73) Assignee: Scan Technology Co., Ltd., Tokyo (JP)

( * ) Notice: Subject to any disclaimer, the term of this patent is extended or adjusted under 35 U.S.C. 154(b) by 0 days.

(21) Appl. No.: 10/251,258

(22) Filed: Sep. 19, 2002

(65) Prior Publication Data

US 2003/0214649 A1 Nov. 20, 2003

(30) Foreign Application Priority Data

May 14, 2002 (JP) .......................................... 2002-137886

(51) Int. Cl.[7] .............................................. G01N 21/00
(52) U.S. Cl. ..................... 356/240; 356/239.1; 250/223
(58) Field of Search ................. 356/437, 440, 356/239.1, 239.4, 239.5, 240.1; 250/223

(56) References Cited

U.S. PATENT DOCUMENTS

| | | | | | |
|---|---|---|---|---|---|
| 4,241,256 | A | * | 12/1980 | Tagaya et al. .......... | 250/223 B |
| 4,367,405 | A | * | 1/1983 | Ford ....................... | 250/223 B |
| 4,402,612 | A | * | 9/1983 | Alexander et al. ....... | 356/239.6 |
| 4,914,289 | A | * | 4/1990 | Nguyen et al. .......... | 356/239.4 |
| 4,943,713 | A | * | 7/1990 | Yoshida .................. | 250/223 B |
| 5,072,108 | A | * | 12/1991 | Ishikawa ................. | 250/223 B |
| 5,256,871 | A | * | 10/1993 | Baldwin .................. | 356/239.4 |
| 5,444,237 | A | * | 8/1995 | Takizawa ................ | 250/223 B |
| 5,489,692 | A | * | 2/1996 | Hirschmann et al. ....... | 548/519 |
| 5,495,330 | A | * | 2/1996 | Champaneri et al. .... | 356/240.1 |
| 5,536,935 | A | * | 7/1996 | Klotzsch et al. ........ | 250/223 B |
| 5,591,899 | A | * | 1/1997 | Griesbeck ................ | 356/240.1 |
| 5,661,294 | A | * | 8/1997 | Buchmann et al. ......... | 209/526 |
| 5,864,395 | A | * | 1/1999 | Laurberg ................. | 356/239.6 |
| 5,905,595 | A | * | 5/1999 | Minami ................... | 356/241.1 |
| 5,926,268 | A | * | 7/1999 | Bonewitz et al. ........ | 356/240.1 |
| 6,067,155 | A | * | 5/2000 | Ringlien .................. | 356/240.1 |
| 6,175,107 | B1 | * | 1/2001 | Juvinall .................... | 356/239.4 |
| 2003/0142299 | A1 | * | 7/2003 | Kwirandt ................. | 356/239.5 |

FOREIGN PATENT DOCUMENTS

JP       2002-221498      8/2002

* cited by examiner

Primary Examiner—Michael P. Stafira
Assistant Examiner—Juan D. Valentin, II
(74) Attorney, Agent, or Firm—Ladas & Parry

(57) ABSTRACT

In an inspecting apparatus for a foreign matter for detecting a foreign matter got entered an object being inspected that contains a liquid product by inspecting the object being inspected optically with imaging means, a conical prism is disposed between the object being inspected and the imaging means. Consequently, it is possible to provide an inspecting apparatus for a foreign matter for use in a production line for manufacturing liquid products, such as drinks and liquid drugs, which can detect in a reliable manner whether a foreign matter has entered a liquid inside a container, such as a bottle or a PET bottle, and a foreign matter in a colored bottle or PET bottle or in a colored liquid as well.

26 Claims, 13 Drawing Sheets

INSPECTING APPARATUS FOR FOREIGN MATTER

BACKGROUND OF THE INVENTION

1. Field of the Invention

The present invention relates to an inspecting apparatus for a foreign matter (impurities) for detecting a foreign matter got entered a liquid product (including a fluid product), such as drinks and liquid drugs, and more particularly to an inspecting apparatus for a foreign matter achieving high-speed and highly accurate inspection by providing a conical prism at imaging means end at the time of inspection, so that a shape at the bottom portion of a container where a foreign matter is most likely to deposit is magnified while at the same time an entire area subject to inspection is pictured.

2. Description of the Related Art

Adoption of the HACCP (Hazard Analysis Critical Control Point) system to the Food Sanitation Law and enforcement of the PL (Product Liability) Law in recent years have been making it mandatory to further ensure the product safety by forestalling a hazard, such as microbial contamination and entrance of foreign matters like metal, fabrics, hair, etc., that could occur in any stage from manufacturing/processing of products, such as food and drugs, to consumption by end consumers through storage/distribution of the products.

HACCP is a hazard analysis and critical control point system established in the United States and is highly evaluated across the world as a sanitary control system method. The HACCP system is a science-based sanitary control system in which product safety is addressed throughout the manufacturing procedure so that preventive measures in the manufacturing procedure are emphasized in contrast to a conventional sanitary control system in which inspection of final products is emphasized. The HACCP system includes two sections: hazard analysis (HA) and critical control point (CCP), and it further ensures the product safety by forestalling an occurrence of a hazard in the manufacturing procedure without overlooking any possibility by (1) checking/analyzing a hazard, such as microbial contamination, that could occur in any stage from manufacturing/processing of food to consumption by end consumers through storage/distribution of the products and setting critical control points to prevent the hazard, (2) setting the criteria of control and constantly monitoring whether the critical limit is being met by checking the records of control, and (3) managing and controlling hazards of other natures with a pre-requisite program (PP).

In a mass-production line of a manufacturing factory, workers detect foreign matters got entered liquids filled in containers by visual inspection. However, such visual inspection is conducted on spot-check basis that one in every certain number of containers is picked up and inspected. Hence, there is a problem that it is by no means reliable inspection conducted for each individual product.

In the case of a method on one hundred percent inspection basis by deploying inspectors along the production line, relatively large foreign matters can be detected by the visual inspection, but minute foreign matters cannot be detected, which raises a problem that the detection is less accurate. Also, the ability of the visual inspection of the inspectors is no longer comparable to an increasing speed of the production line, and it is true that the inspection efficiency is becoming poor. Further, the visual inspection has no effect on colored liquids, such as coffee or cola, and there has been a need for a countermeasure.

As an inspecting method for a foreign matter got entered a liquid solution filled in a container other than the visual inspection, the container may be pictured from the outside by an inspection camera, so that the presence or absence of non-conformity is detected based on image information thus obtained. However, in order to allow the containers of the liquid product to stand upright firmly, the concavity at the bottom portion is deepened from the center to the outside, and a foreign matter in the liquid is most likely to deposit at the deepest concaved bottom portion. Hence, it is effective to picture chiefly such a portion at the time of inspection. FIGS. 1A and 1B and FIGS. 2A and 2B show the foregoing state. FIG. 1A is a side view showing the bottom portion of a PET bottle 100 with a foreign matter 101 deposited on the bottom portion, and FIG. 1B is a bottom view thereof. FIG. 2A is a side view showing the bottom portion of a PET bottle 102 with a foreign matter 103 deposited on the bottom portion, and FIG. 2B is a bottom view thereof.

As a method for magnifying an image of an arbitrary portion, a zoom mechanism or the like may be provided to the optical system to picture an image. However, when the zoom mechanism magnifies a specified portion, it also magnifies the entire object being inspected at the same magnification. Thus, there is a portion that goes out the range of the optical system installed to match with the actual size of the object being inspected. This makes it impossible to inspect the entire area subject to inspection, thereby raising a problem that the reliability is lowered.

FIG. 3 is a view showing an example of an optical detecting apparatus, in which a PET bottle 111 as an object being inspected is irradiated by a light source 110 so that transmitted light from the bottom portion of the PET bottle 111 is received by a CCD sensor 120, and a light reception signal from the CCD sensor 120 is subjected to image processing by a data processing apparatus (not shown), whereby a foreign matter 113 got entered a liquid product 112 inside the PET bottle 111 and deposited at the bottom thereof is detected.

According to the inspecting apparatus arranged as above, in order to utilize the optical system effectively, the detection is conducted by matching the maximum diameter of the PET bottle 111 with a full size 130 of the optical system as shown in FIG. 4. In other words, because the foreign matter 113 needs to be magnified as large as possible for the detection, the maximum diameter of the PET bottle 111 is set to the full size 130 of the optical system. Hence, the size of the detected foreign matter on the image depends on the magnification of the optical system defined by the full size 130. The accuracy of inspection is improved by detecting the foreign matter at the larger magnification. Thus, when the foreign matter is magnified for the detection, only the image has to be enlarged by providing a zoom mechanism to the optical system. However, as shown in FIG. 5, the zoom mechanism also magnifies the entire pictured region at the same magnification (characteristic A of FIG. 17), and the entire object being inspected does not come within the range of the optical system. A portion 111A indicated by a broken line of FIG. 5 shows a portion that goes out from the range of the optical system. Hence, there may be a case that a region where a foreign matter is present goes out from an inspection screen. This raises a problem that a foreign matter cannot be detected in a reliable manner.

A method of magnifying an arbitrary portion by editing a pictured image with software may be proposed. However, because an inspection time per container is too long, this method is not suitable for use in a high-speed mass-production line for the drinks or liquid drugs, thereby raising a problem that the manufacturing yield is lowered.

Additionally, the conventional inspecting apparatus is not able to detect a foreign matter by an optical method or irradiation of laser beams when a colored translucent PET bottle or bottle is filled with a transparent liquid, or when a transparent PET bottle or bottle is filled with a colored liquid, such as coffee, juice or cola. A foreign matter may be detected with X-rays when the container is opaque or translucent. However, the X-rays per se have ill effects on the human body; moreover, a large-scale and fairly expensive apparatus needs to be installed.

For this reason, the inspection of a bottle or a PET bottle for a foreign matter has not been conducted at all once a colored liquid product is filled therein. However, in order to attain the perfection of the product, there has been a need to conduct the inspection of bottles or PET bottles for the foreign matters in a reliable manner whether the liquids are transparent or colored.

SUMMARY OF THE INVENTION

The present invention is devised in view of the foregoing, and has an object to provide an inspecting apparatus for a foreign matter for use in a production line for manufacturing liquid products, such as drinks and liquid drugs, which can detect in a reliable manner whether a foreign matter has entered a liquid inside a container, such as a bottle and a PET bottle, and a foreign matter in a colored bottle or PET bottle or in a colored liquid as well.

The present invention relates to an inspecting apparatus for detecting if foreign matter entered an object that contains a liquid being inspected optically with imaging means, and the object of the present invention is achieved by disposing a conical prism between the object being inspected and the imaging means.

The object of the present invention is achieved more effectively by arranging in such a manner that: the conical prism is a single-side conical prism; the conical prism is a double-side conical prism; the imaging means is a CCD sensor; the liquid product and the object being inspected are transparent, and the foreign matter is one of a suspended foreign matter and a deposited foreign matter; or the object being inspected is one of a bottle and a PET bottle.

The present invention relates to an inspecting apparatus for detecting foreign matter entered an object that contains a liquid being inspected optically with imaging means, and the object of the present invention is achieved by arranging in such a manner that light radiated through to the object being inspected is an infrared light having a wavelength of 750 to 1000 nm; and a conical prism is disposed between the object being inspected and the imaging means.

The object of the present invention is achieved more effectively by arranging in such a manner that: the infrared light is irradiated at power in a range from 0.7 mW to 100 W both inclusive; the conical prism is a single-side conical prism; the conical prism is a double-side conical prism; the imaging means is a CCD sensor; one or both of the liquid product and the object being inspected are colored, opaque, or translucent; or the object being inspected is one of a bottle and a PET bottle.

BRIEF DESCRIPTION OF THE DRAWINGS

The above and other objects will become more apparent when preferred embodiments of the invention are considered in connection with the drawings, in which.

DETAILED DESCRIPTION OF THE PREFERRED EMBODIMENTS

According to the present invention, in a production line for manufacturing liquid products (including fluid products), such as drinks and liquid drugs, whether a foreign matter (either suspended or deposited), such as metal, fabrics, hair or dust, has entered a bottle or a PET bottle is detected by using infrared light or a CCD sensor with a local magnifying function of a conical prism. In particular, it is possible to detect a foreign matter got entered the liquid in a reliable manner without stopping the production line by using the magnifying function of the conical prism even when the liquid product is a colored liquid, such as coffee, cola, juice or milk, or even when a translucent or colored bottle or a PET bottle is filled with a transparent liquid product, such as mineral water. In other words, according to the invention, a site where a foreign matter is present is magnified locally and the foreign matter is detected stably in a reliable manner, so that a foreign matter entering during the manufacturing/processing procedure of the product, including, for example, a raw material foreign matter that cannot be removed by inspection of the raw materials, an environmental foreign matter that would possibly enter upon placement on the production line, and a manufacturing machine foreign matter entering from the manufacturing machine itself during the manufacturing, is detected in a reliable manner in the final stage and a non-conforming product containing a foreign matter is removed in a reliable manner.

The following description will describe embodiments of the present invention with reference to the accompanying drawings.

Figures 1A, 1B:
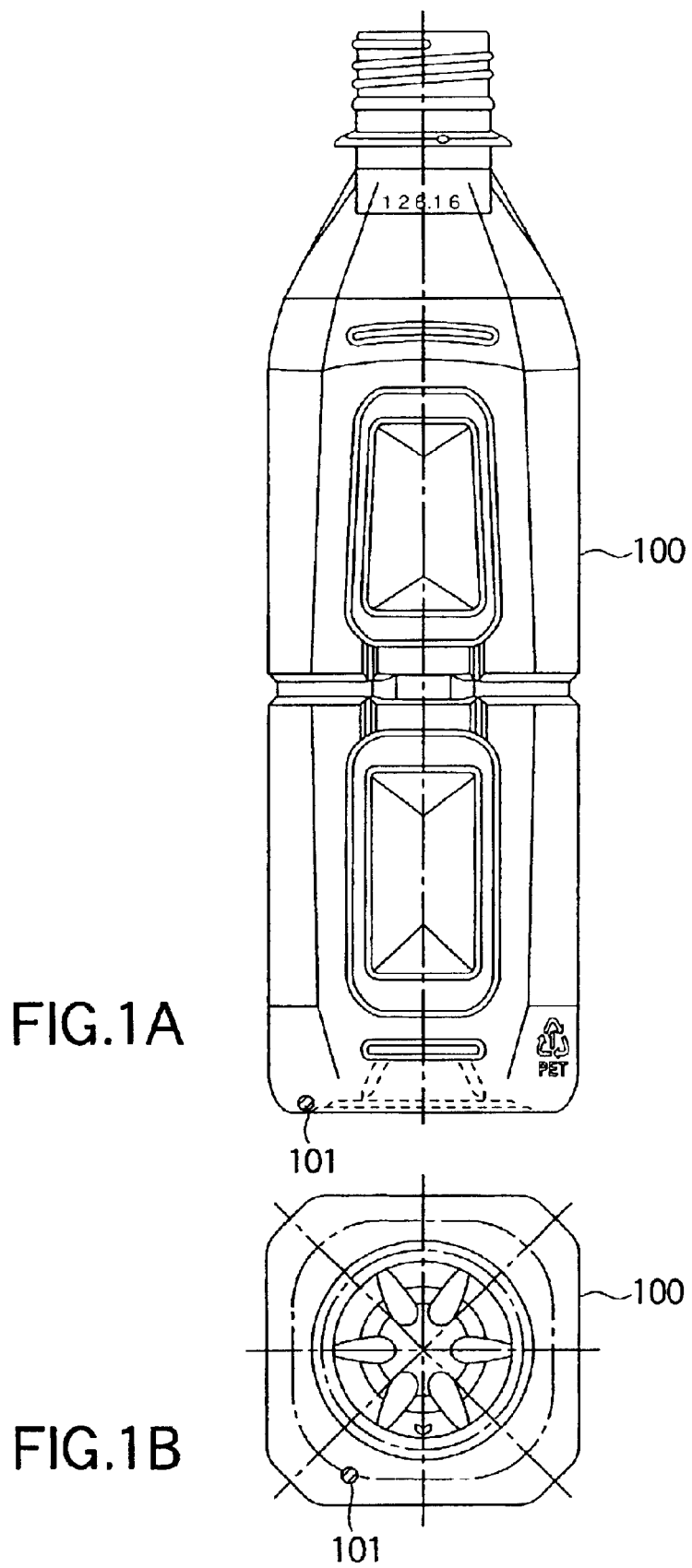
FIGS. 1A and 1B are respectively a side view and a bottom view explaining a structure of the bottom portion of a PET bottle and how a foreign matter deposits.
Figures 2A, 2B:
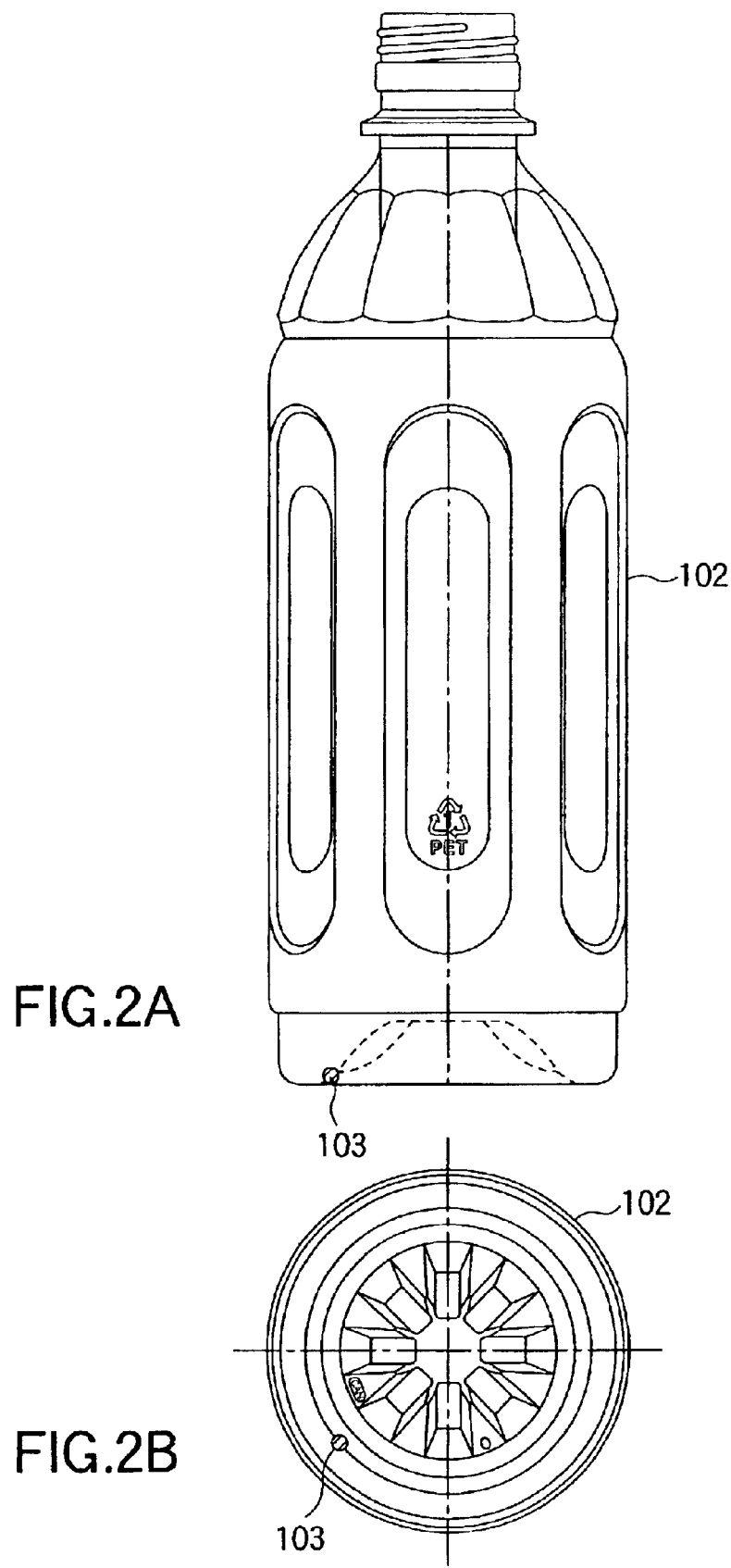
FIGS. 2A and 2B are respectively a side view and a bottom view explaining a structure of the bottom portion of a PET bottle and how a foreign matter deposits.
Figure 3:
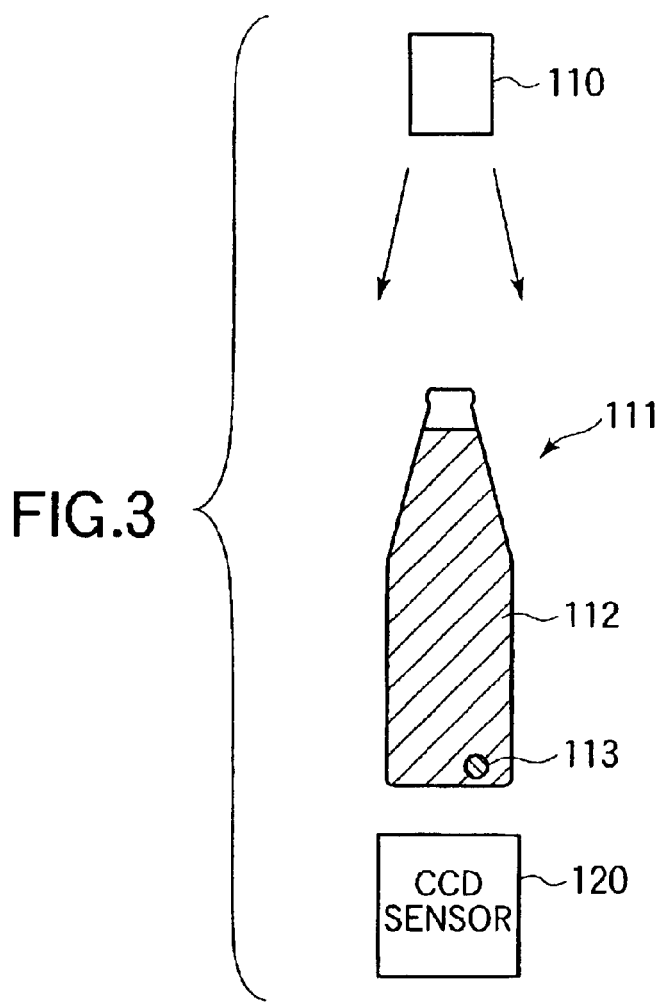
FIG. 3 is a view showing an example of a conventional optical detecting apparatus.
Figure 4:
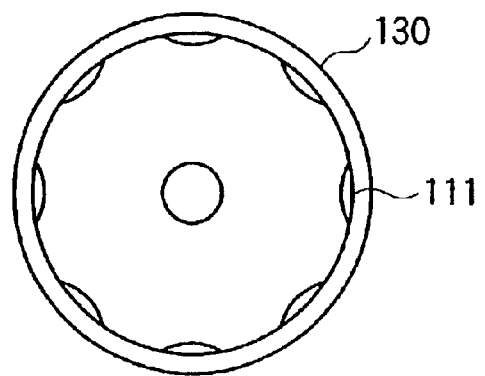
FIG. 4 is a view explaining an optical system in the conventional detecting apparatus.
Figure 5:
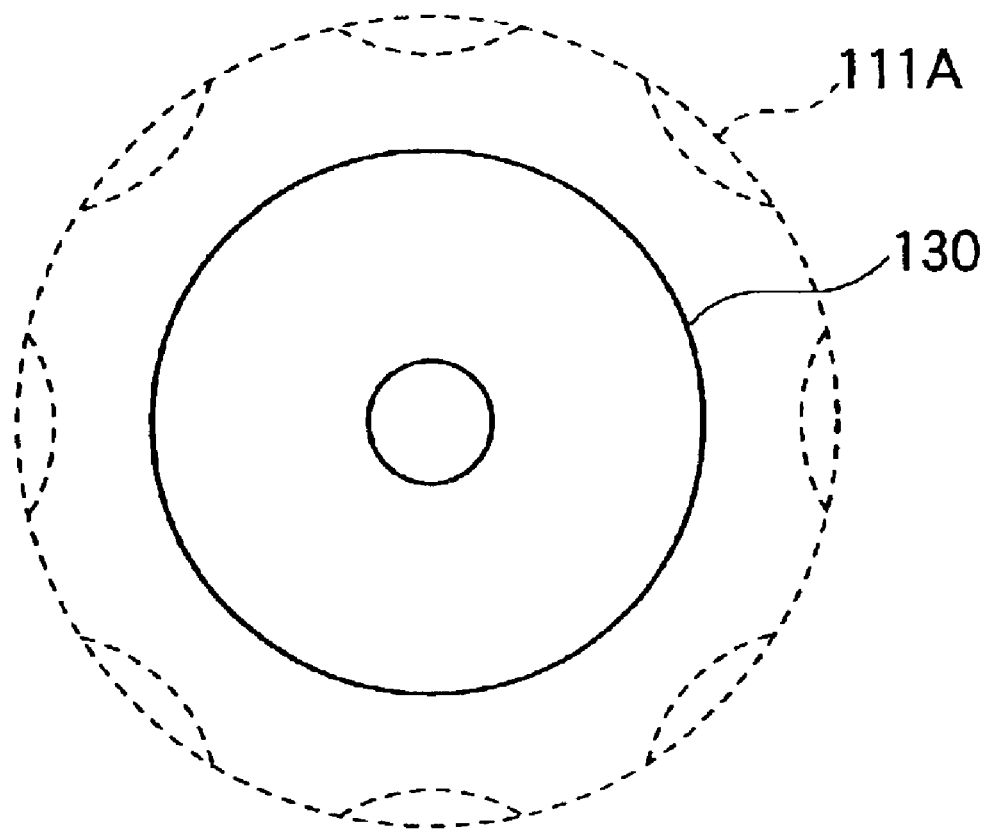
FIG. 5 is another view explaining the optical system in the conventional detecting apparatus.
Figure 6:
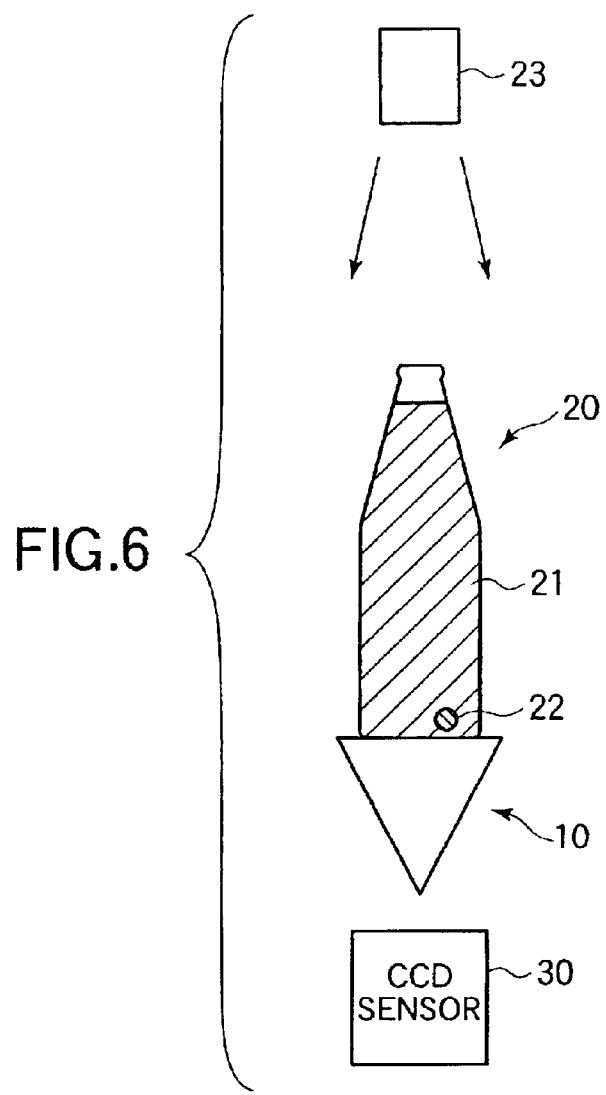
FIG. 6 is a view showing a basic arrangement according to one embodiment of the present invention.
Figure 7:
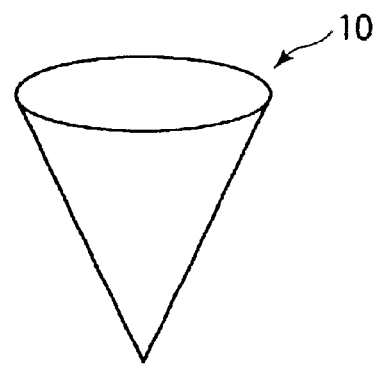
FIG. 7 is a perspective view showing a structure of a single-side conical prism.

FIG. 6 is a view showing a basic arrangement of an inspecting apparatus for a foreign matter of the present invention. Assume that a PET bottle 20 as an object being inspected is filled with a liquid (for example, water, drops, etc.) 21, and a foreign matter 22 has entered the liquid 21. A light source 23 is provided above the PET bottle 20, and a CCD (Charge-Coupled Device) sensor 30 is provided under the bottom portion of the PET bottle 20 through a single-side conical prism 10. The single-side conical prism 10 is of a structure shown in FIG. 7 and is made of transparent glass, quartz, etc.

By disposing the single-side conical prism 10 between the PET bottle 20 and the CCD sensor 30 in this manner, the bottom portion of the PET bottle 20 is magnified locally, thereby making it possible to detect the foreign matter 22 being magnified. Consequently, accuracy in inspection for a foreign matter can be improved.

Figure 8:
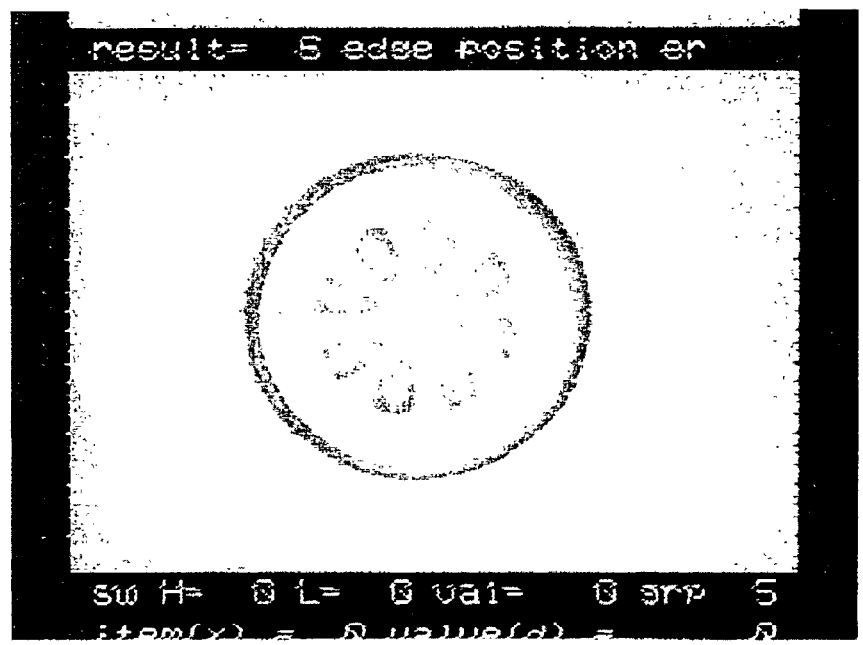
FIG. 8 is a view showing an example of an image pictured by a CCD sensor.
Figure 9:
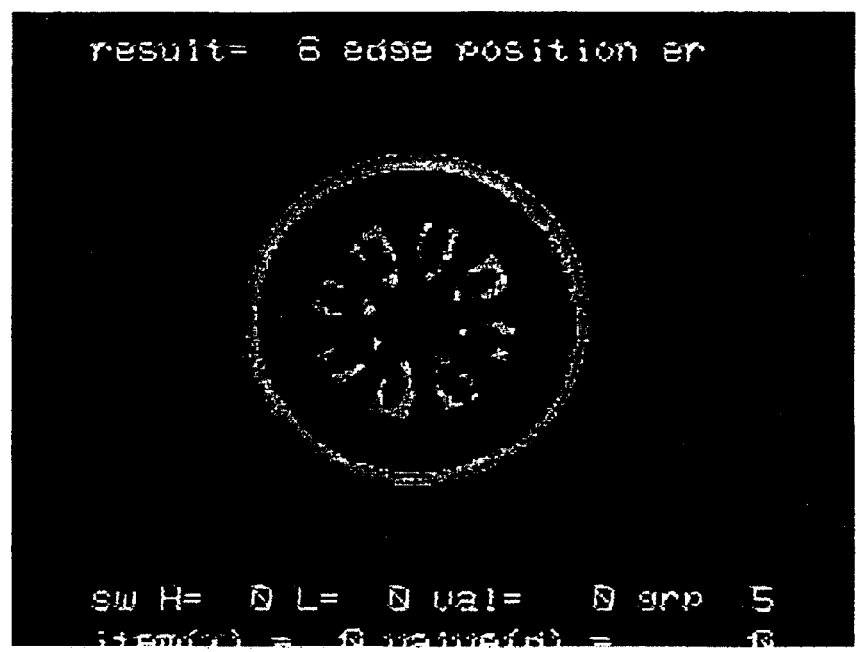
FIG. 9 is a view showing a binary image of FIG. 8.
Figure 10:
FIG. 10 is a view showing an example of an image pictured by the CCD sensor when the single-side conical prism is disposed.
Figure 11:
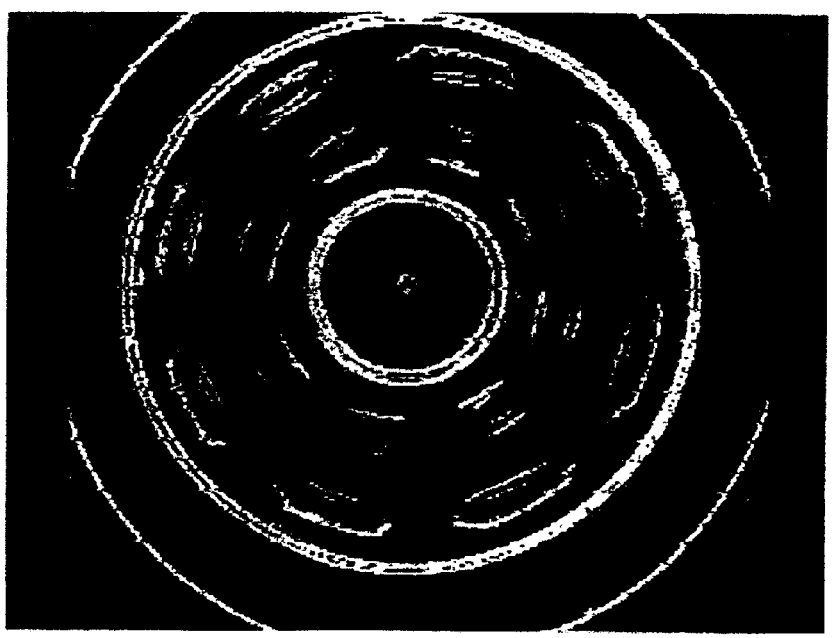
FIG. 11 is a view showing a binary image of FIG. 10.

FIG. 8 is a view showing an image pictured by the CCD sensor 30 when the single-side conical prism 10 is not disposed, and FIG. 9 is a view showing a binary image of the pictured image. In comparison, by disposing the single-side conical prism 10 between the CCD sensor 30 and the PET bottle 20, a pictured image as shown in FIG. 10 is obtained, and the pictured image is converted into a binary image as shown in FIG. 11. The actual image data in the latter two drawings confirms the improvement of the accuracy in inspection for a foreign matter.

Figure 12:
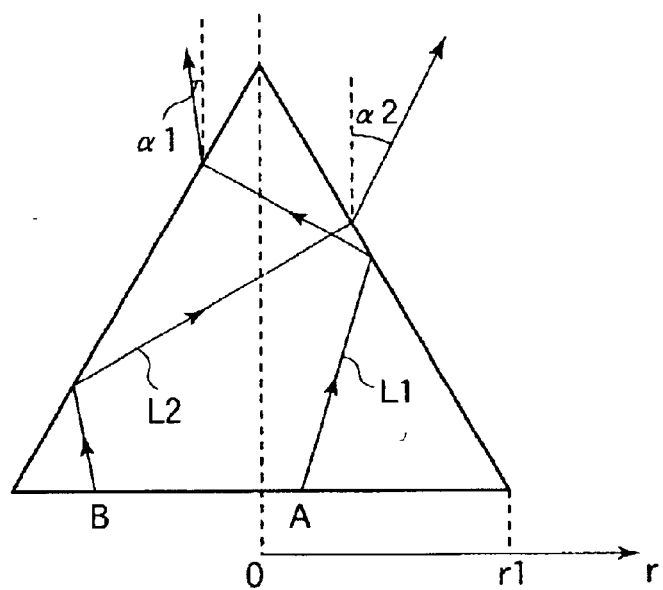
FIG. 12 is a view showing an example of an optical path from the single-side conical prism.
Figure 13:
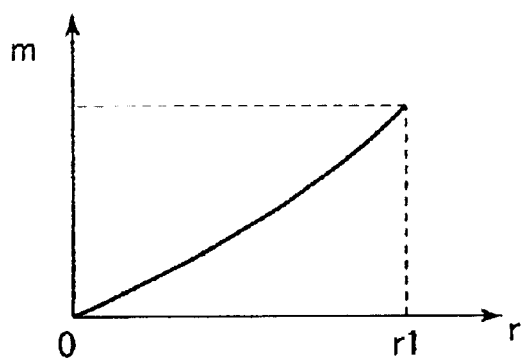
FIG. 13 is a view showing a distribution of magnification of the single-side conical prism.
Figure 17:
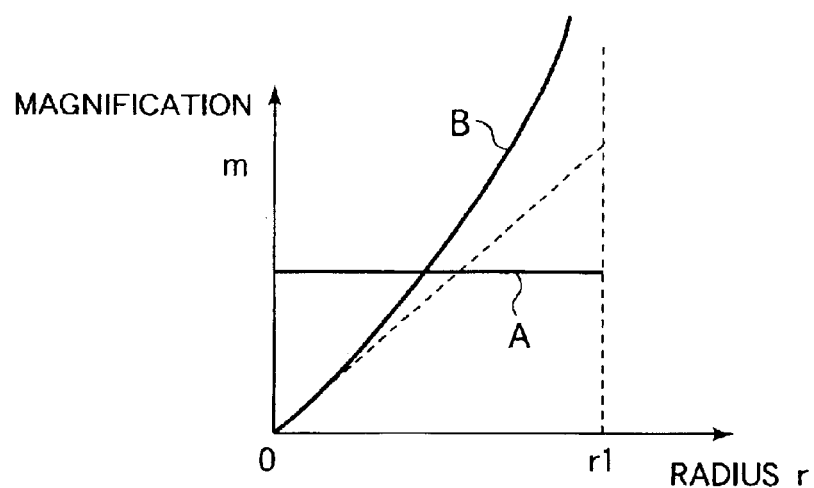
FIG. 17 is a view showing a distribution of magnification of the double-side conical prism.

It is assumed that the single-side conical prism 10 takes an optical path as shown in FIG. 12 with respect to the flat bottom portion. To be more specific, an optical path passing a given point (for example a point A) in close proximity to the central portion "0" of the cone is a path L1 that goes out at a small irradiation angle $\alpha 1$, whereas an optical path passing a given point (for example, a point B) remote from the central portion "0" of the cone is a path L2 that goes out at a large irradiation angle $\alpha 2$. A small irradiation angle $\alpha$ means a small magnification "m" for magnifying the image of the bottom portion, and a large irradiation angle $\alpha$ means a large magnification "m" for magnifying the image of the bottom portion. Hence, a relation between a distance r from the central portion "0" of the cone to a given point and the magnification m is the one as shown in FIG. 13, which reveals that the magnification m becomes larger as a given point moves away from the central portion 0 of the cone. Therefore, this relation is different from the relation of the zoom mechanism that magnification is constant for any given point (characteristic A of FIG. 17).

Figure 14:
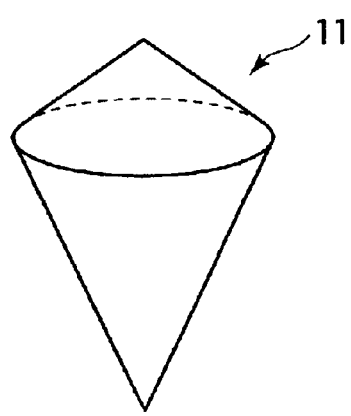
FIG. 14 is a perspective view showing a structure of a double-side conical prism.
Figure 15:
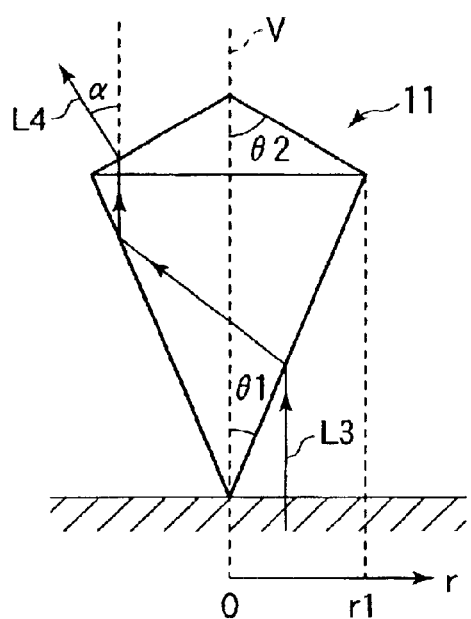
FIG. 15 is a view showing an example of an optical path from the double-side conical prism.
Figure 16:
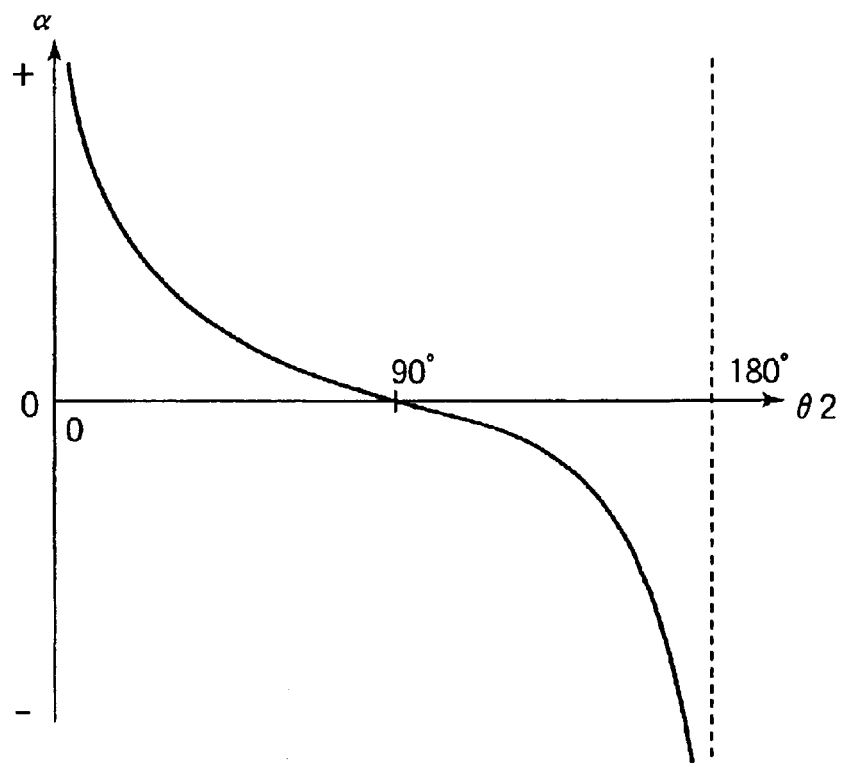
FIG. 16 is a view showing an example of a characteristic of the double-side conical prism.

As shown in FIG. 14, by adding a conical prism on the top of the conical prism 10 described above and thereby making a double-side conical prism 11, the optical path, that is, outgoing light L4 goes out with a tilt at an angle $\alpha$ as shown in FIG. 15. Given $\theta 1$ and $\theta 2$ as the prism angles respectively at the lower face and at the upper face of the double-side conical prism 11, and angle $\alpha$ as an outgoing angle of the outgoing light L4, then the characteristic as shown in FIG. 16 is obtained. To be more specific, the prism angle $\theta 1$ does not depend on the outgoing angle $\alpha$ and varies with the prism angle $\theta 2$. The outgoing angle $\alpha$ becomes 0 when 90° is given as the prism angle $\theta 2$, and it becomes infinite at the positive side when 0° is given as the prism angle $\theta 2$ while it becomes infinite at the negative side when 180° is given as the prism angle $\theta 2$.

Hence, by setting the prism angle $\theta 2$ in a range, $0° < \theta 2 < 90°$, an image magnified as desired can be obtained. Given r1 as a radius value of the maximum diameter of the double-side conical prism 11, then the magnification "m" from the tip of the prism (radius=0) to the radius r1 varies in a quadric manner as indicated by a characteristic B of FIG. 17, which is different from the characteristic A of the zoom mechanism that keeps constant magnification. More specifically, in the case of using the zoom mechanism for magnification, as is indicated by the characteristic A, the magnification is constant at any given point from the center position (radius=0) to the outside (radius r), whereas in the case of using the double-side conical prism 11, as is indicated by the characteristic B, the magnification m, which is 0 at the center position (radius=0), increases gradually toward the outside. Hence, it is possible to detect a foreign matter by magnifying locally a desired portion of the object being inspected alone without magnifying the entire object being inspected as is in the conventional method.

Figure 18:
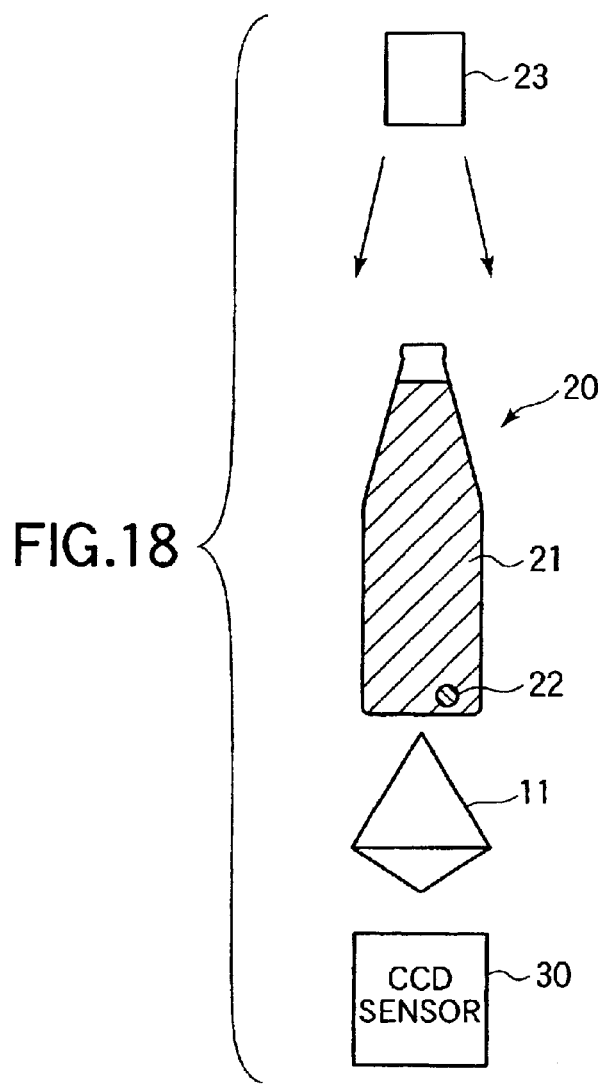
FIG. 18 is a view showing an arrangement of another embodiment of the present invention.
Figure 19:
FIG. 19 is a view showing an example of an image pictured by the CCD sensor when the double-side conical prism is disposed.
Figure 20:
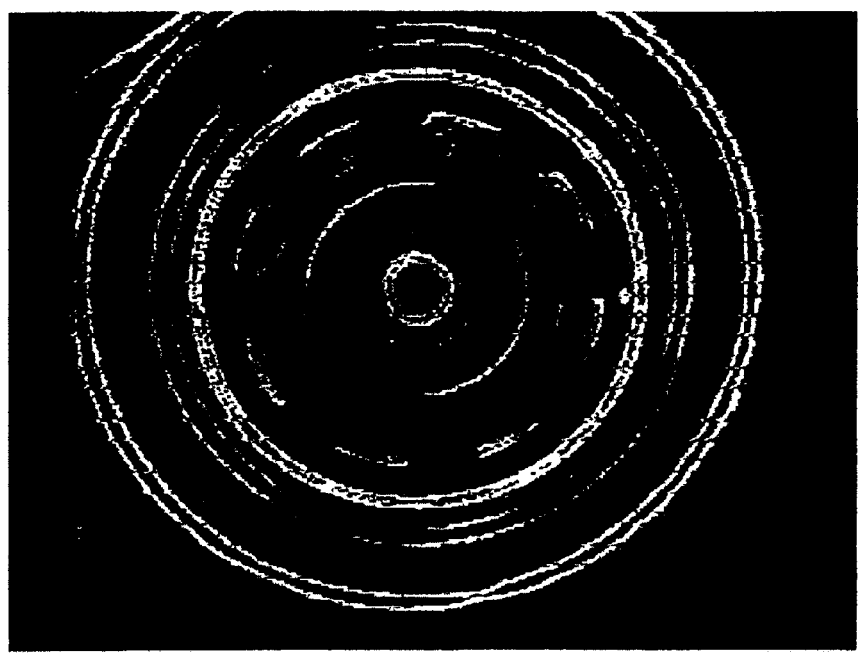
FIG. 20 is a view showing a binary image of FIG. 19.

FIG. 18 is a view showing an inspecting apparatus for a foreign matter employing the double-side conical prism 11 as described above in correspondence with FIG. 6. FIG. 19 is a view showing an image pictured by the CCD sensor 30 of this apparatus, and FIG. 20 is a view showing a binary image of the pictured image. The actual image data shown in these drawings also reveals that the foreign matter is magnified larger in the outward concave at the bottom portion of the container where the foreign matter is most likely to deposit.

Figure 21:
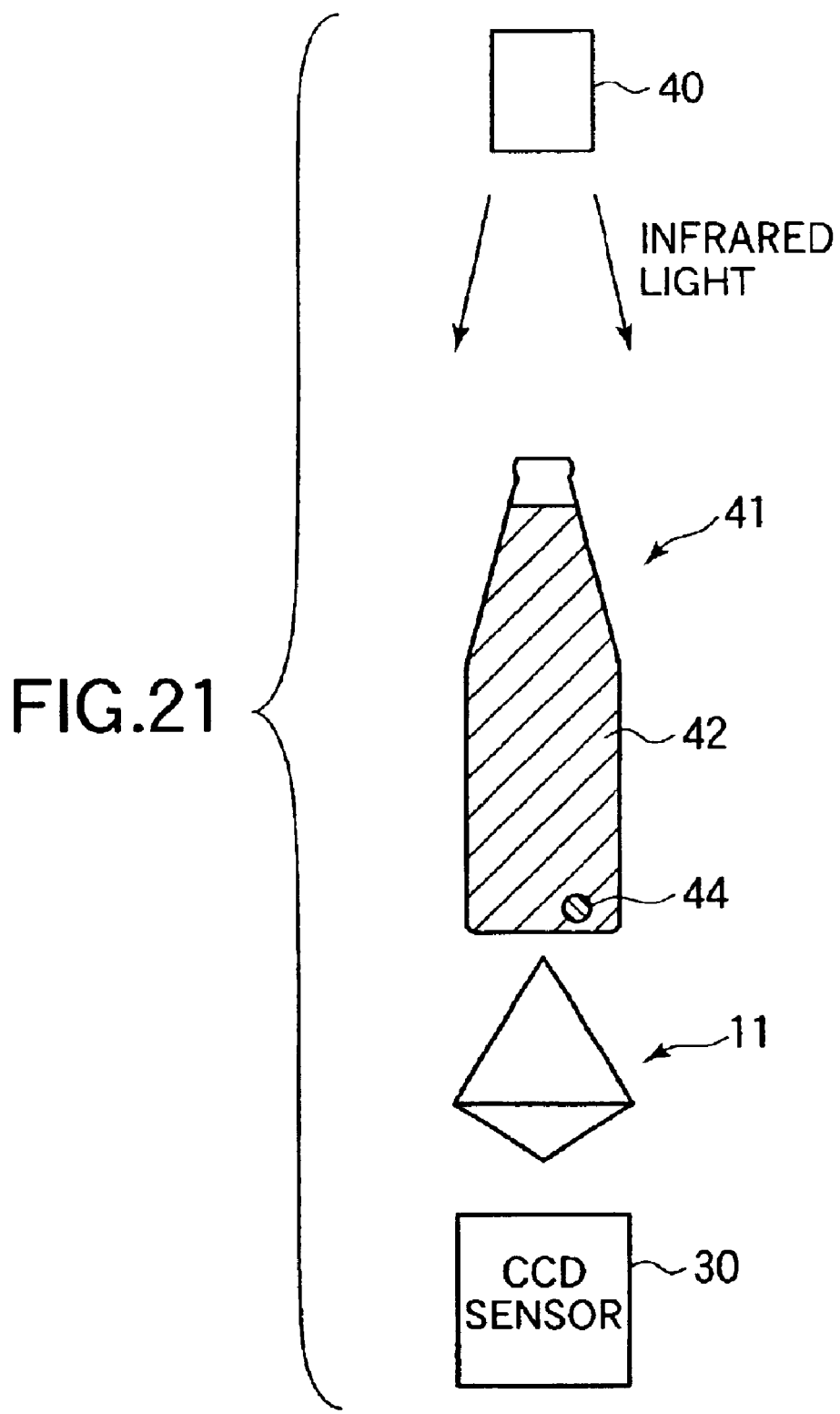
FIG. 21 is a view showing an arrangement of still another embodiment of the present invention.

FIG. 21 is a view showing still another embodiment of the present invention applied to a case where a liquid 42 is a colored liquid, such as coffee, cola or milk, or when a container 41, such as a bottle or a PET bottle, is opaque or translucent. A foreign matter 44 is invisible because of the color of the liquid 42, which makes it difficult to detect the foreign matter 44 by a visual inspection or an optical method. However, it is possible to detect the foreign matter 44 by irradiating infrared light having a wavelength of 750 to 1000 nm from an infrared light source 40 at power in a range from 0.7 mW to 100 W, so that transmitted light from the container 41 is collected by an objective lens (not shown) and received by the CCD sensor 30 (which is described in, for example, Japanese Patent Application Nos. 2000-357665 and 2001-18055 filed by the applicant of the present application). The CCD sensor 30 has wide and high wavelength sensitivity characteristics (ranges of the wavelength and the sensitivity that the photo-receiver can response) covering from blue to near-infrared, thereby having high quantum efficiency in trapping photons. The quantum efficiency of a picture is 2 to 3% at most; however, the quantum efficiency of the CCD sensor 30 is as high as 90%. Also, the CCD sensor 30 is characterized by its large ratio (dynamic range) of the maximum and minimum brightness that can be measured simultaneously and its superior linearity.

It is discovered that, because of these characteristics, the CCD sensor 30 reserves electrons in a packet by exploiting a phenomenon (photoelectric effect) that free electrons are generated when transmitted light impinges on the CCD sensor 30, so that by merely reading out these electrons sequentially after exposure of a certain period, in case that molecules have high light transmittance like an aqueous solution, it turns a colored or solid black aqueous solution into a transparent aqueous solution. The same can be said in a case where a colored container is filled with a transparent aqueous solution.

Figure 22:
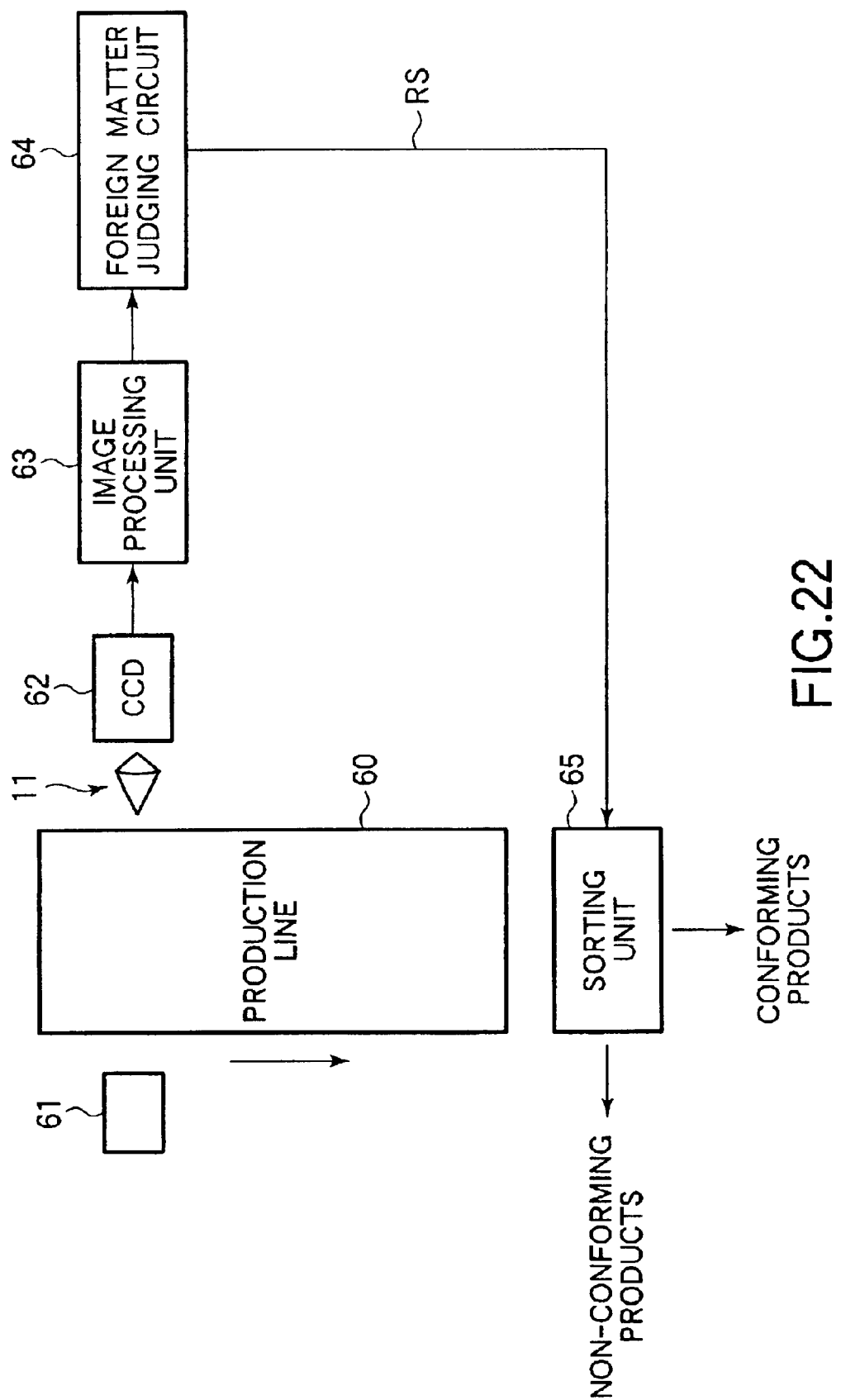
FIG. 22 is a view explaining an application example of the present invention.

Next, the following description will describe an example of the invention when applied to a production line with reference to FIG. 22.

Herein, for example, PET bottles are flowing down on a production line 60, and the PET bottles are irradiated by a light source 61, and transmitted light is received by the double-side conical prism 11 (or the single-side conical prism 10) and a CCD sensor 62 provided at the opposite side. A detection signal from the CCD sensor 62 is subjected to an image processing by an image processing unit 63, and a foreign matter judging circuit 64 judges the presence or absence of a foreign matter. Upon judging the presence of a foreign matter, the foreign matter judging circuit 64 outputs a remove signal RS. The production line 60 is provided with a sorting unit 65 for sorting out the PET bottles, which removes a PET bottle corresponding to the remove signal RS, thereby sorting out conforming products and non-conforming products. Consequently, it is possible to manufacture and ship only the conforming products.

As has been described, according to the present invention, a foreign matter is detected by locally magnifying a screen pictured by the photo-receiving element, which makes it possible to detect the foreign matter in a reliable manner. In the invention, a conical prism provided at the imaging means end is employed at a time of the inspection. Thus, not only can a portion at the bottom of a container where a foreign matter is most likely to deposit due to its shape be magnified, but also the entire area subject to inspection can be pictured at the same time. Consequently, it is possible to detect a foreign matter got entered the container at a high speed and accuracy.

Further, even when a bottle or a PET bottle is filled with a colored liquid or a bottle or a PET bottle is colored, not only can a foreign matter be detected in case it has entered the bottle or PET bottle, but also a non-conforming product containing a foreign matter can be removed. Hence, it is possible to remove any foreign matter that may possibly enter just moments before the final product is manufacture by filling a container, such as a bottle and a PET bottle, with a liquid product, thereby further ensuring the product safety.

Obviously many modifications and variations of the invention are possible in the light of the above teachings. It is therefore to be understood that within the scope of the appended claims in the invention may be practiced otherwise than as specifically described.

What is claimed is:

1. An inspecting apparatus of a foreign matter for detecting the foreign matter contained in a sealed bottle, containing a liquid product, characterized by:
    a light source radiating light from over the top portion of said sealed bottle into said liquid in order to intensify the contrast of light and darkness of the liquid and the foreign matter;
    a conical prism disposed closely to the bottom face of said sealed bottle in order to enlarge said foreign matter;
    an imaging means disposed under said conical prism, intensifying the contrast of light and darkness of said liquid and the foreign matter and also obtaining an enlarged image of the foreign matter in said liquid by receiving the light through said conical prism from said light source and passing through said liquid; and
    a detecting means detecting the foreign matter contained in said sealed bottle containing the foreign matter in the liquid deposited in the concavity of the inside bottom portion of said sealed battle by processing signals of said images including all area of the bottom face of said sealed bottle obtained by said imaging means.

2. The inspecting apparatus according to claim 1, wherein said conical prism is a single-side conical prism.

3. The inspecting apparatus according to claim 1, wherein said conical prism is a double-side conical prism.

4. The inspecting apparatus according to claim 2, wherein said imaging means is a CCD sensor.

5. The inspecting apparatus according to claim 3, wherein said imaging means is a CCD sensor.

6. The inspecting apparatus according to claim 1, wherein said liquid product and said sealed bottle being inspected are transparent, and said foreign matter is one of a suspended foreign matter and a deposited foreign matter.

7. The inspecting apparatus according to claim 6, wherein said sealed bottle being inspected is one of a bottle and a PET bottle.

8. An inspecting apparatus of a foreign matter for detecting the foreign matter contained in a sealed bottle containing a liquid product, characterized by:
    a light source radiating light having a wavelength of 750 to 1000 nm wavelength from over the top portion of said sealed bottle into said liquid in order to intensify the contrast of light and darkness of the liquid and the foreign matter;
    a conical prism disposed closely to the bottom face of said sealed bottle in order to enlarge said foreign matter;
    an imaging means disposed under said conical prism, intensifying the contrast of light and darkness of said liquid and the foreign matter and also obtaining an enlarged image of the foreign matter in said liquid by receiving the light through said conical prism from said light source and passing through said liquid; and
    a detecting means detecting the foreign matter contained in said sealed bottle containing the foreign matter in the liquid deposited in the concavity of the inside bottom portion of said sealed bottle by processing signals of said images including all area of the bottom face of said sealed bottle obtained by said imaging means.

9. The inspecting apparatus according to claim 8, wherein said light is radiated at power in a range from 0.7 mW to 100 W both inclusive.

10. The inspecting apparatus 8, wherein said conical prism is a single-side conical prism.

11. The inspecting apparatus according to claim 8, wherein said conical prism is a double-side conical prism.

12. The inspecting apparatus according to claim 8, wherein said imaging means is a CCD sensor.

13. The inspecting apparatus according to claim 8, wherein one or both of said liquid product and said sealed bottle being inspected are colored, opaque or translucent.

14. The inspecting apparatus according to claim 8, wherein said sealed bottle being inspected is one of a bottle and a PET bottle.

15. The inspecting apparatus according to claim 9, wherein said conical prism is a single-side conical prism.

16. The inspecting apparatus according to claim 8, wherein said conical prism is a double-side conical prism.

17. A process for detecting a foreign matter in a sealed bottle containing a liquid product, characterized by:

radiating light from over the top portion of said sealed bottle into said liquid in order to intensify the contrast of light and darkness of the liquid and the foreign matter;

enlarging said foreign matter by a conical prism disposed closely to the bottom face of said sealed bottle in order to enlarge said foreign matter;

intensifying the contrast of light and darkness of said liquid and the foreign matter and also obtaining an enlarged image of the foreign matter in said liquid by receiving the light through said conical prism from said light source and passing through said liquid by an imaging means disposed under said conical prism; and detecting a foreign matter contained in said sealed bottle containing foreign matters in the liquid deposited in the concavity of the inside bottom portion of said sealed bottle by processing signals of said images, by a detecting means, including all area of the bottom face of said sealed bottle obtained by said imaging means.

18. The process according to claim 17 wherein said light has a wavelength of 750 to 1000 nm.

19. The process according to claim 18, wherein said light has a power in a range from 0.7 mW to 100 W.

20. The process according to claim 17, wherein said conical prism is a single-side conical prism.

21. The process according to claim 17, wherein said conical prism is a double-side conical prism.

22. The process according to claim 20, wherein said imaging means is a CCD sensor.

23. The process according to claim 21, wherein said imaging means is a CCD sensor.

24. The process according to claim 17, wherein said liquid product and said sealed bottle being inspected are transparent, and said foreign matter is one of a suspended foreign matter and a deposited foreign matter.

25. The process according to claim 18, wherein one or both of said liquid product and said sealed bottle being inspected are colored, opaque or translucent.

26. The process according to claim 17, wherein said sealed bottle being inspected is one of a bottle and a PET bottle.

* * * * *